(12) United States Patent
Feng et al.

(10) Patent No.: US 6,958,038 B2
(45) Date of Patent: Oct. 25, 2005

(54) MULTIPOSITIONAL RATCHET DEVICE FOR SURGICAL RETRACTOR

(75) Inventors: David Feng, Arlington Heights, IL (US); Joseph Hirt, Mundelein, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/969,935

(22) Filed: Oct. 2, 2001

(65) Prior Publication Data

US 2003/0065251 A1 Apr. 3, 2003

(51) Int. Cl.$^7$ .............................................. A61B 17/02
(52) U.S. Cl. ........................ 600/228; 600/233; 600/234
(58) Field of Search ................................ 600/201, 215, 600/234, 227, 228; 74/575, 577 M, 577 R, 577 S

(56) References Cited

U.S. PATENT DOCUMENTS

| | | | |
|---|---|---|---|
| 3,749,088 A | 7/1973 | Kohlmann | 128/20 |
| 4,421,108 A * | 12/1983 | Cabrera et al. | 600/234 |
| 4,424,724 A | 1/1984 | Bookwalter et al. | 74/540 |
| 5,375,481 A | 12/1994 | Cabrera et al. | 74/577 |
| 5,667,481 A | 9/1997 | Villalta et al. | 600/224 |
| D397,791 S | 9/1998 | Koros et al. | D24/135 |
| 5,951,466 A | 9/1999 | Segermark et al. | 600/225 |
| 5,976,080 A | 11/1999 | Farascioni | 600/213 |
| 6,042,542 A * | 3/2000 | Koros et al. | 600/231 |
| 6,053,908 A | 4/2000 | Crainich et al. | 606/1 |
| 6,241,659 B1 * | 6/2001 | Bookwalter et al. | 600/231 |
| 6,431,025 B1 * | 8/2002 | Koros et al. | 74/577 M |
| 6,537,212 B2 | 3/2003 | Sherts et al. | 600/205 |
| 2001/0007052 A1 | 7/2001 | Person | 600/231 |
| 2002/0152833 A1 * | 10/2002 | Phillips | 74/575 |

* cited by examiner

Primary Examiner—Cary E. O'Connor
(74) Attorney, Agent, or Firm—Andrew G. Rozycki

(57) ABSTRACT

The invention disclosed herein relates to a multipositional ratchet device for use in conjunction with a surgical retractor assembly. The ratchet device of the invention permits both independent and simultaneous adjustment of the longitudinal axial positioning of a retractor blade stem relative to the device as well as the vertical tilt position of the retractor blade. Furthermore, the device is structured with the adjustment tabs positioned to permit the aforementioned adjustments using continuously maintained finger contact on the tabs using a single hand. The device affords the user improved ergonomics and accuracy of use by virtue of its structural and functional features.

4 Claims, 15 Drawing Sheets

MULTIPOSITIONAL RATCHET DEVICE FOR SURGICAL RETRACTOR

FIELD OF THE INVENTION

The invention relates to the field of medical devices used in surgical procedures. In particular, the invention pertains to adjustable mechanisms associated with surgical retractor devices.

BACKGROUND OF THE INVENTION

Surgical retractors are often used in surgical procedures wherein relatively larger areas of access to surgical sites are required, and wherein retention and clearance of surrounding tissues is needed. A variety of surgical retractor assemblies are known in the art. Typically, retractor blades include stems which are secured or fastened to a frame which is positioned surrounding the surgical site.

The ability to position and secure retractor blades into fixed position or easily reposition or adjust the position during the surgical procedure has been a desirable feature in retractor assemblies. In certain surgical procedures, in addition to circumferential positioning of the retractor blades surrounding a surgical site, it is also advantageous to control the longitudinal adjustment of the retractor blade for opening and restraining tissue surrounding the surgical site. Even more advantageous is the ability to control the angle at which the retractor blades and stem are positioned relative to the surgical site and retractor support assembly, or relative "tilt angle".

Adjustable surgical retractor mechanisms which attach to ring assemblies and permit longitudinal adjustment of the retractor blade stem as well as tilting adjustment are disclosed in Bookwalter et al. U.S. Pat. No. 4,424,724; Cabrera et al. U.S. Pat. No. 5,375,481 and Koros et al. U.S. Pat. No. Des. 397,791. The ratchet mechanisms described in Bookwalter et al. and Koros et al., however, permit separate longitudinal and tilting adjustments and require a certain degree of maneuvering and repositioning of the fingers and hands to operate. The mechanism described in Cabrera et al. operates such that actuation of one adjustment mechanism necessarily actuates another. None of these devices offer the practitioner the collective ability to individually or simultaneously adjust the tilt and/or longitudinal setting of the ratchet device in an ergonomically comfortable, non-awkward manner.

There exists a need in the medical field for improved retractor devices which permit the practitioner to freely and easily adjust and re-adjust the positioning of the retractor blade during a procedure in an accurate, non-awkward and non-cumbersome manner. There is a further need for surgical retractor assemblies and associated mechanisms to have improved ergonomic attributes.

SUMMARY OF THE INVENTION

The invention provides for an ergonomically and functionally improved ratchet device for use in conjunction with a retractor blade and retractor support assembly. More particularly, the ratchet device of the invention permits both independent and simultaneous adjustment of the longitudinal axial positioning of a retractor stem and blade, as well as the tilt or angled position of the retractor stem and blade. It has been discovered that a ratchet device for a surgical retractor can be structured to contain adjustment tabs which permit the aforementioned adjustments while also permitting a continuous finger contact position on the tabs and device using a single hand. Accordingly, awkward or unnecessary maneuvering and repositioning of the hand and fingers to adjust the retractor positions is avoided. Both the longitudinal axial positioning of the retractor blade stem and vertical tilt positioning of the retractor are accomplished using a natural manual "pinching" movement of the user's hand and fingers, without physically obstructing or interfering with the other components of the retractor assembly.

The invention provides a multipositional ratchet device for use in conjunction with a surgical retractor comprising:
  a) a housing adapted to accommodate a portion of a retractor blade stem, said housing having a front end and rear end and two opposing sides, a movable portion movably coupled to a support portion;
  b) tilt adjustment mechanism mechanically coupled to said housing and adapted to control the vertical tilt position of said movable portion of housing relative to said support portion of housing;
  c) longitudinal adjustment mechanism mechanically coupled to said housing and adapted to control the longitudinal axial positioning of said retractor blade stem relative to said housing;
    wherein said tilt adjustment mechanism comprises a tilt adjustment tab and said longitudinal adjustment mechanism comprises a longitudinal adjustment tab, said adjustment tabs permitting both independent and simultaneous tilt and longitudinal adjustments respectively using continuously maintained finger contact thereon by a single hand throughout said adjustment;
    and wherein said tilt adjustment tab and longitudinal adjustment tab are located on the same side of said housing.

In an alternative embodiment, the invention provides a multipositional ratchet device for use in conjunction with a surgical retractor comprising:
  a) a housing adapted to accommodate a portion of a retractor blade stem, said housing having a front end and rear end and two opposing sides, a movable portion movably coupled to a support portion;
  b) tilt adjustment mechanism mechanically coupled to said housing and adapted to control the vertical tilt position of said movable portion of housing relative to said support portion of housing;
  c) longitudinal adjustment mechanism mechanically coupled to said housing and adapted to control the longitudinal axial positioning of said retractor blade stem portion relative to said housing;
    wherein said tilt adjustment mechanism comprises a tilt adjustment tab and said longitudinal adjustment mechanism comprises a longitudinal adjustment tab, said adjustment tabs permitting both independent and simultaneous tilt and longitudinal adjustments respectively using continuously maintained finger contact thereon by a single hand throughout said adjustment;
    and wherein said tilt adjustment tab and longitudinal adjustment tab are located on opposing sides of said housing.

DETAILED DESCRIPTION OF THE INVENTION

Figure 1:
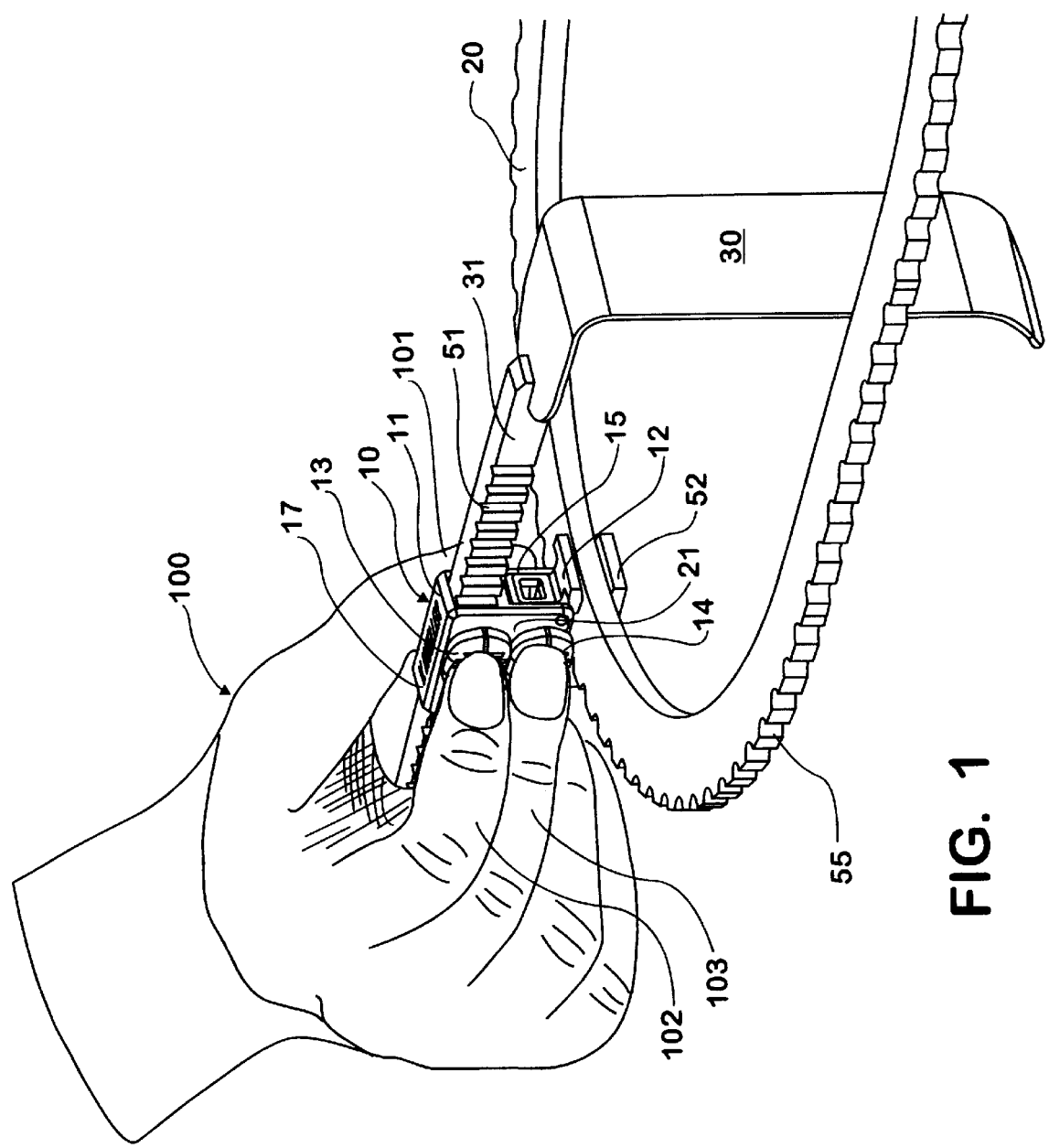
FIG. 1 is an overall perspective view of the device as being operated by a human hand according to one embodiment of the invention, the device shown attached to both a retractor blade and retractor support structure.

The term "multipositional" as used herein refers to the ability to alter the position of at least two portions of the device of the invention relative to one another. The device of the invention permits repositioning along the retractor support structure, angular tilt repositioning and longitudinal repositioning of the retractor stem within.

The term "tabs" as used herein is intended to encompass any component that is adapted for finger contact wherein said finger contact initiates a motion which permits adjustment of the mechanism corresponding to the component.

As used herein, the term "longitudinal adjustment" and inflections thereof refer to the axial movement of the retractor blade stem as inserted through the device of the invention and which can be adjusted and secured by the device. The longitudinal adjustment is the alteration of the position that corresponds to degree of tissue restraint affected by the retractor blade as attached to the retractor support assembly.

The term "tilt adjustment" and inflections thereof refer to the angular movement of the device in the vertical direction relative to a fixed reference point to which a portion of the device is attached, such as the retractor support assembly.

The tilt adjustment is the altering of angular position of the retractor blade and stem relative to the retractor support assembly. In a ring-type retractor support assembly, the tilt is the angular positioning of the retractor stem relative to the generally planar configuration of the ring structure.

The term "ratchet" when used in the context of the device of the invention refers to the incremental adjustment capabilities of the device as is associated with ratchet structures. The term is not intended to imply limitation as to a specific structure which functions to permit said incremental adjustment.

The multipositional ratchet device of the invention is adapted for use with a surgical retractor assembly. Surgical retractor assembly components can include a retractor support assembly to which retractor blades are attached. Typically, the support assembly is a frame-like structured adapted to surround the surgical site. One example of a retractor support assembly which can be used with the device of the invention is a planar ring structure which is positioned circumscribing or surrounding the surgical access site. Accordingly, the ratchet device of the invention includes a portion which is positioned and secured onto the support assembly.

Referring to the figures, the device of the invention generally comprises a housing 10 comprising a movable portion 11 coupled by a hinging structure to a support portion 12. The movable portion 11 of the housing 10 is movable relative to the support portion 12 and comprises a longitudinal adjustment mechanism mechanically coupled to a longitudinal adjustment tab 13, and a tilt adjustment mechanism mechanically coupled to a tilt adjustment tab 14. The support portion 12 of the housing 10 is used to secure the device onto a retractor support structure 20 (shown in FIGS. 1, 2 and 3 as a frame having a ring configuration) of a retractor support assembly. The longitudinal adjustment tab 13 and tilt adjustment tab 14 are positioned on the movable portion 11 of the housing so as to permit both aforementioned adjustments to be made using continuous finger contact position on the tabs and in accordance with single handed operation of the device (see FIG. 1).

Figure 11:
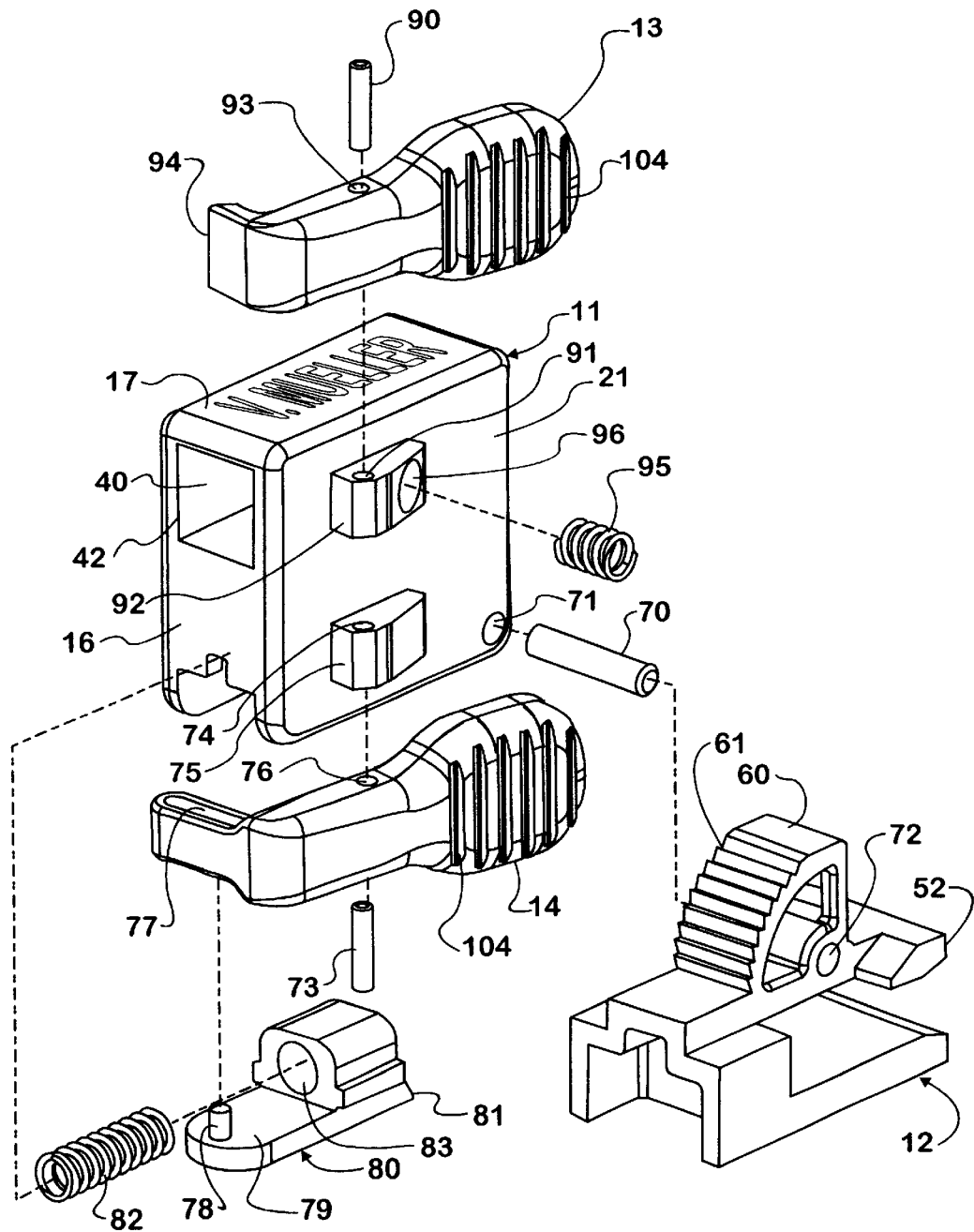
FIG. 11 is an exploded view of the device showing the individual components according to one embodiment of the invention.
Figure 12:
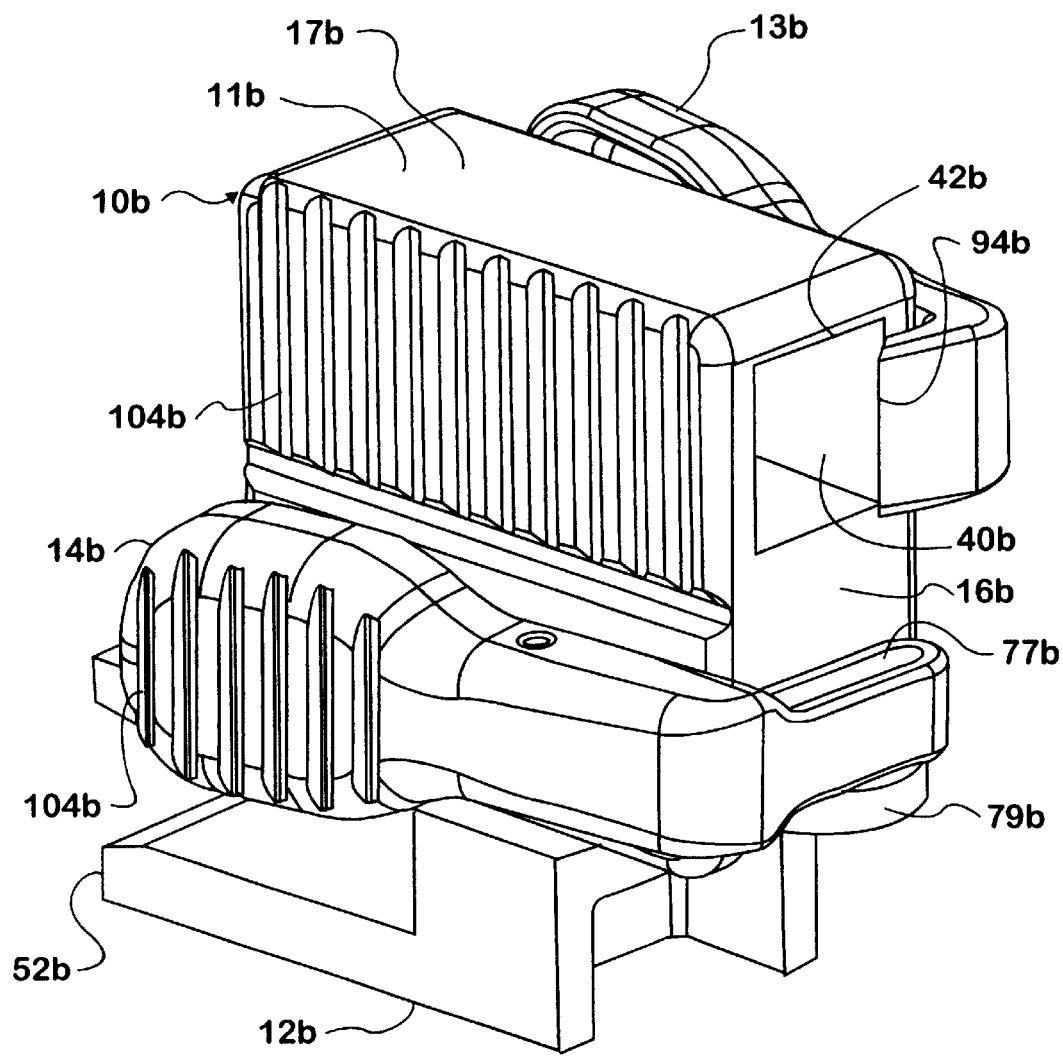
FIG. 12 is an angled side view from the rear of the device according to another embodiment of the invention having adjustment tabs on opposing sides.
Figure 13:
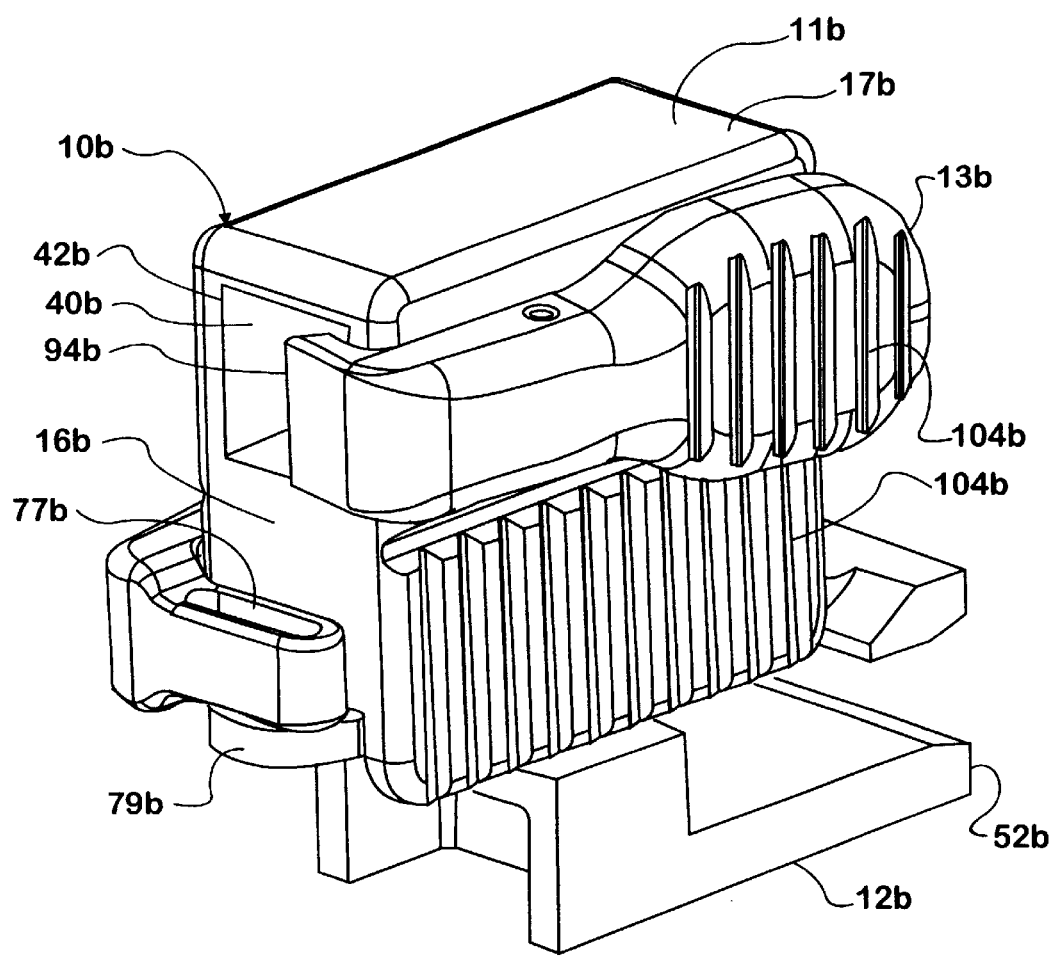
FIG. 13 is an angled side view from the rear of the device of the opposing side to that shown in FIG. 12 according to another embodiment of the invention.
Figure 14:
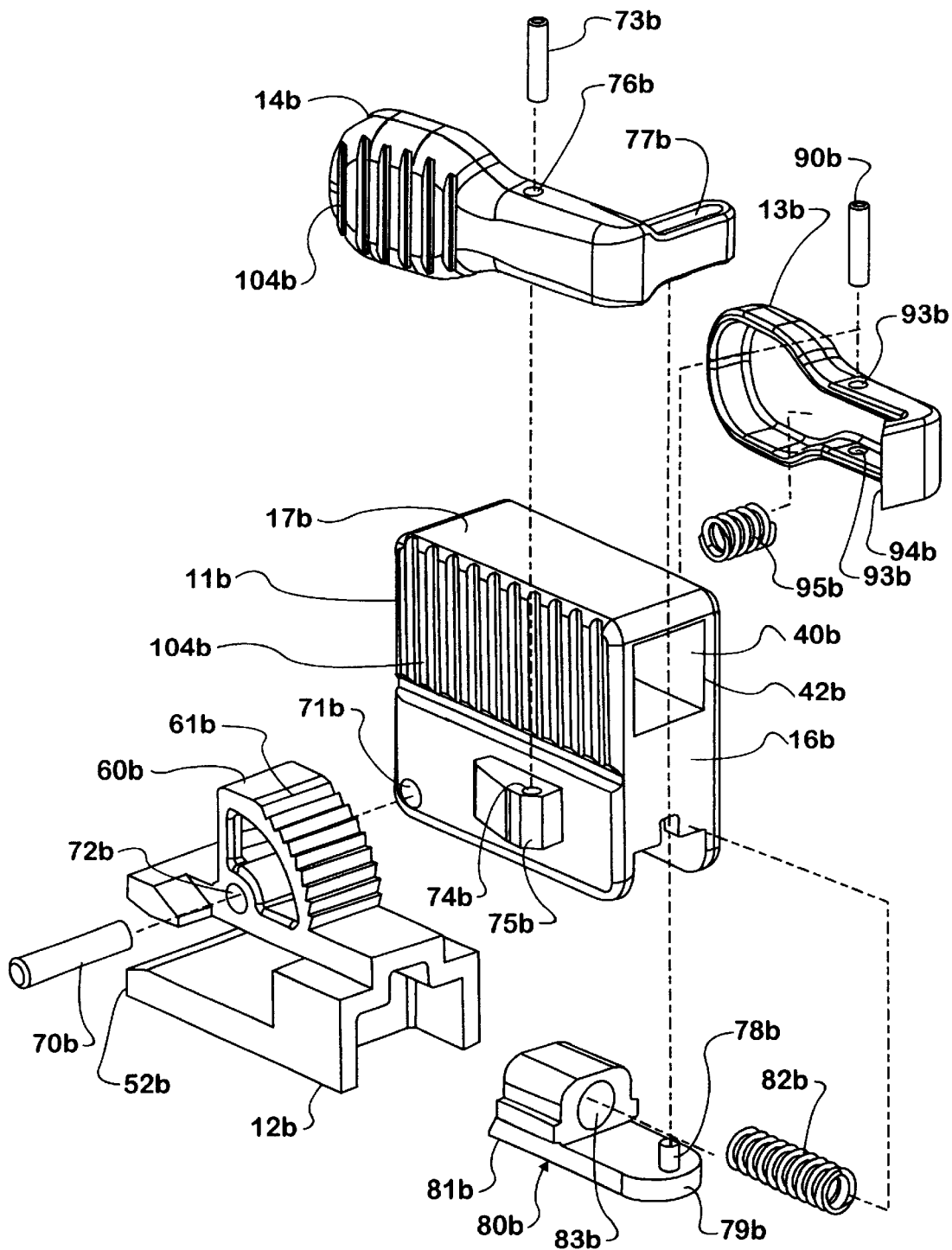
FIG. 14 is an exploded view of the device showing individual components according to another embodiment of the invention having adjustment tabs on opposing sides.

Both adjustment tabs can be located on same side (as shown in FIGS. 1 through 11 and 15A and 15B) or, in an alternative embodiment, opposing sides of housing (as shown in FIGS. 12 through 14). In the preferred embodiment, the adjustment tabs are both located on the same side of the housing. In either configuration, the natural "pinching" and relatively comfortable positioning of the human hand is used to operate the device and perform longitudinal or tilt adjustments either independently or simultaneously. The device contains the structural and functional advantage of affording to the user the capability to perform these two adjustments of the device (aside from positioning the device along the retractor support structure) using a single hand, maintaining continuous unbroken finger contact on the tabs, and offer the option of performing these two adjustments one at a time or simultaneously. Furthermore, the hand and finger position can be maintained continuously while repositioning the device together with the retractor blade 30 attached to the device on the retractor support structure 20 to another blade orientation circumscribing the surgery site. Multidirectional tactile feedback and resistance can be sensed during the adjustments and positioning as a result of the motional freedom offered by the device of the invention. In addition to freeing the users other hand to perform other functions, such as grasp the retractor blade, the device allows the user to easily and quickly accomplish a precise and accurate position of the retractor blade within the surgical access site of the patient.

Referring again to FIG. 1, a user's hand 100 is shown operating the device of the invention. Accordingly, with the thumb 101 positioned on the opposing side of the housing, the index and middle fingers of the user's hand, 102 and 103 respectively, are positioned in a comfortable, non-contorting manner on the longitudinal and tilt adjustment tabs, 13 and 14 respectively. This natural hand position can be maintained throughout the longitudinal and tilt adjustment phase of setting up the retractor assembly for the surgical procedure. This same hand position can also move the device together with the blade laterally along the retractor support structure 20 as well. In an alternative embodiment where the tabs are located on opposing sides of the housing of the device, the same hand configuration likewise operates the device, with the difference being that the thumb operates one of the tabs located on the opposing side.

The finger-contacting surfaces of the adjustment tabs can further comprise surface treatment, texturing, and/or contouring to facilitate gripping and operation of the device. Any suitable topographical modification adapted to enhance contact and handling of the device can be used. Suitable treatment or texturing which can be used includes, but is not limited to, patterned or unpatterned serrations, ridges, grooves, pebbling, roughening, and the like. Suitable contouring includes providing a concave topography to the finger contoured surface compatible with the natural curvature of the human fingertip. The exterior surface of the housing can be surface treated, textured, or modified as well. In the figures, both tabs and a portion of the exterior of the housing are shown containing a series of parallel ridges 104 to facilitate grip.

In a further embodiment, the exterior surface of the housing and/or tabs can comprise apparent or visible indicia. For example, such indicia can reveal the action corresponding to each tab for the practitioner's guidance. A variety of indicia can be used, including but not limited to, symbols, words, abbreviations, colors, and the like. Indicia can be created by any conventional technique appropriate for medical devices, such as printing, etching or molding techniques.

Referring now to FIGS. 4 through 10, the movable portion 11 and support portion 12 of the housing 10 of the device comprise a front side 15 (see FIG. 8), rear side 16 (see FIG. 9), top side 17 (see FIG. 10) and bottom side 18, and a first and second opposing sides, 21 and 22 respectively. Within the context of FIGS. 1 through 11, the first side 21 of the device comprises a tilt adjustment tab 14 and a longitudinal adjustment tab 13 located together on the movable portion 11 of the housing 10.

Figure 2:
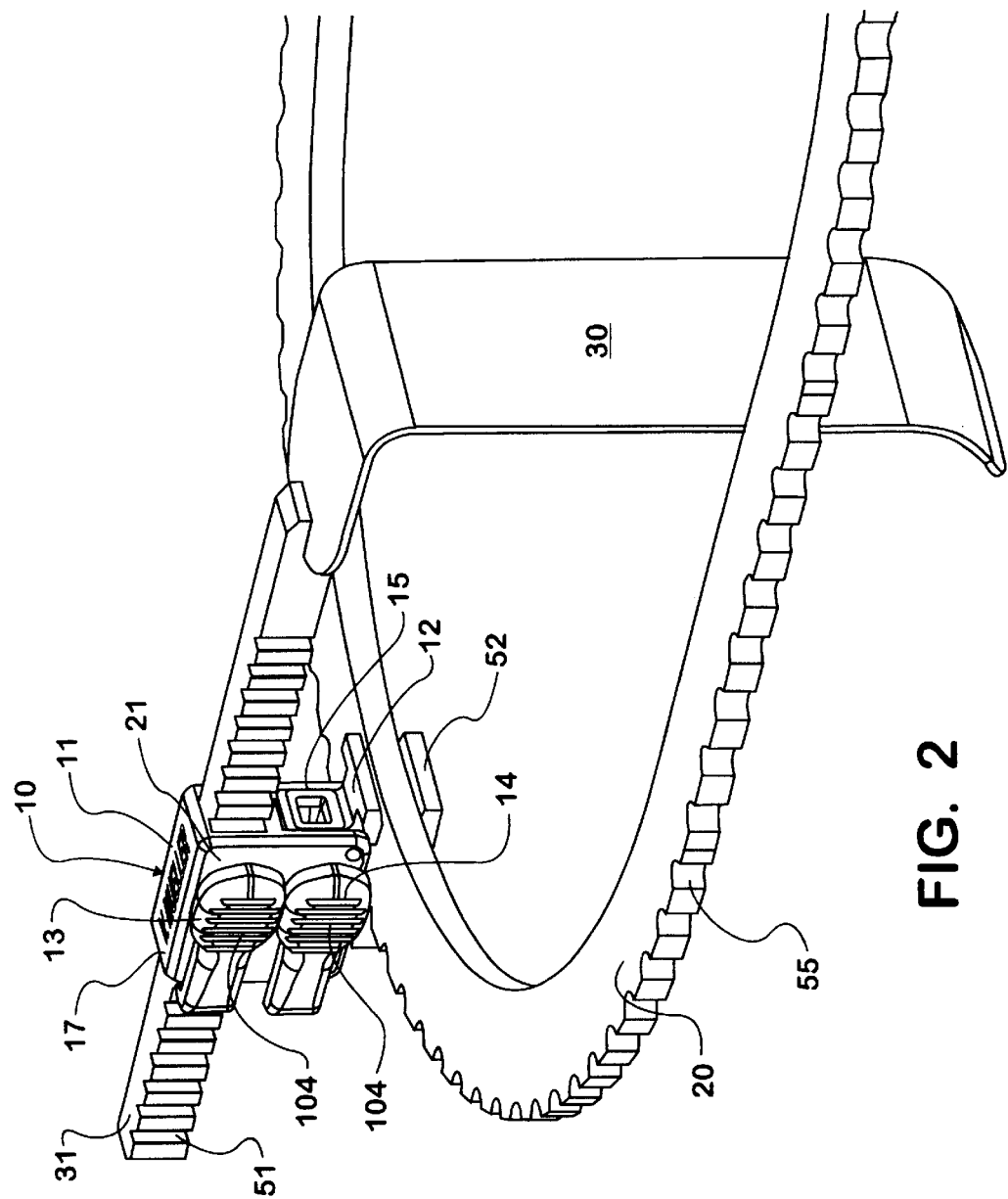
FIG. 2 is an angled side view of the device attached to a retractor blade and support structure according to one embodiment of the invention.
Figure 3:
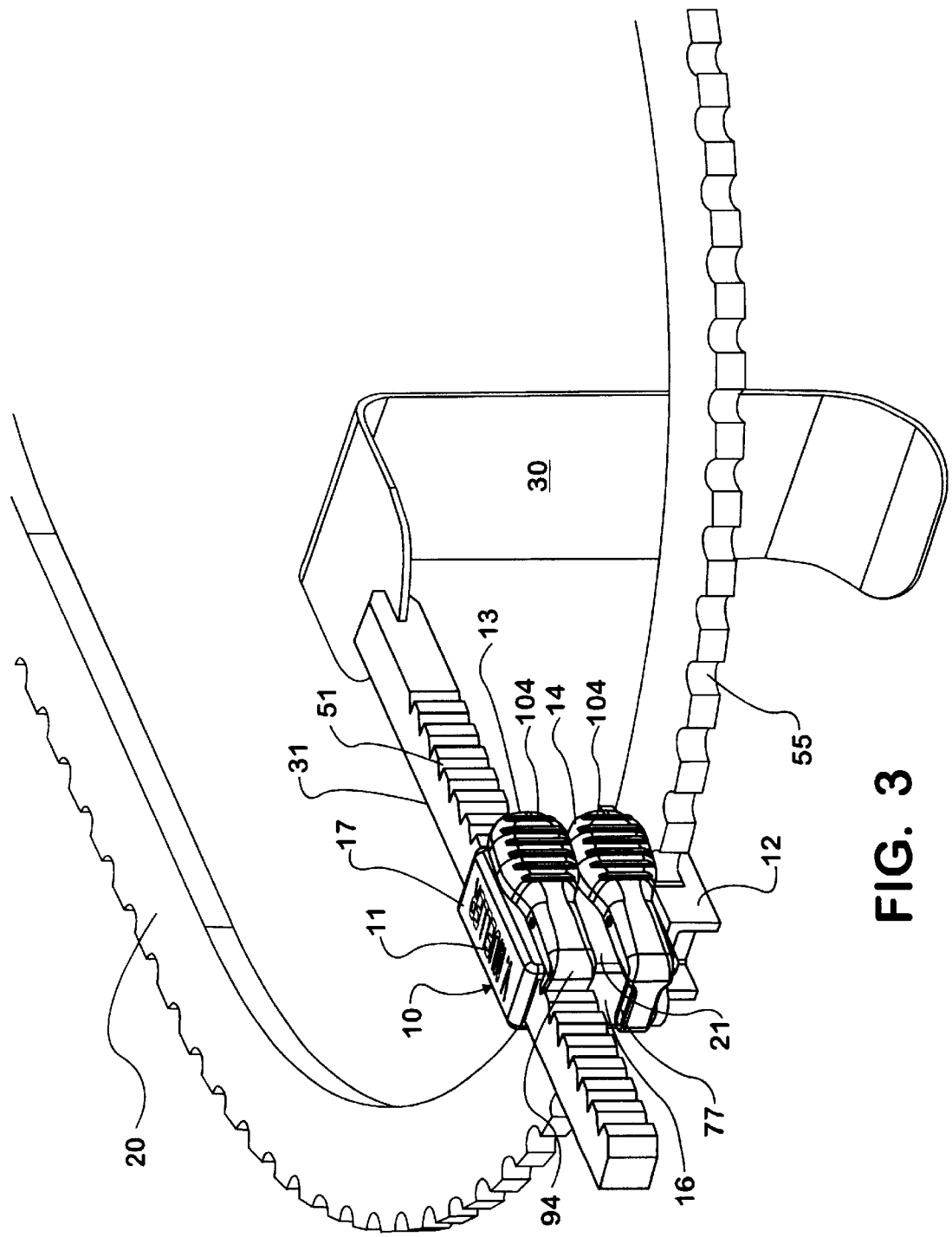
FIG. 3 is an angled side view as approached from the rear of the device attached to a retractor blade and support structure according to one embodiment of the invention.
Figure 4:
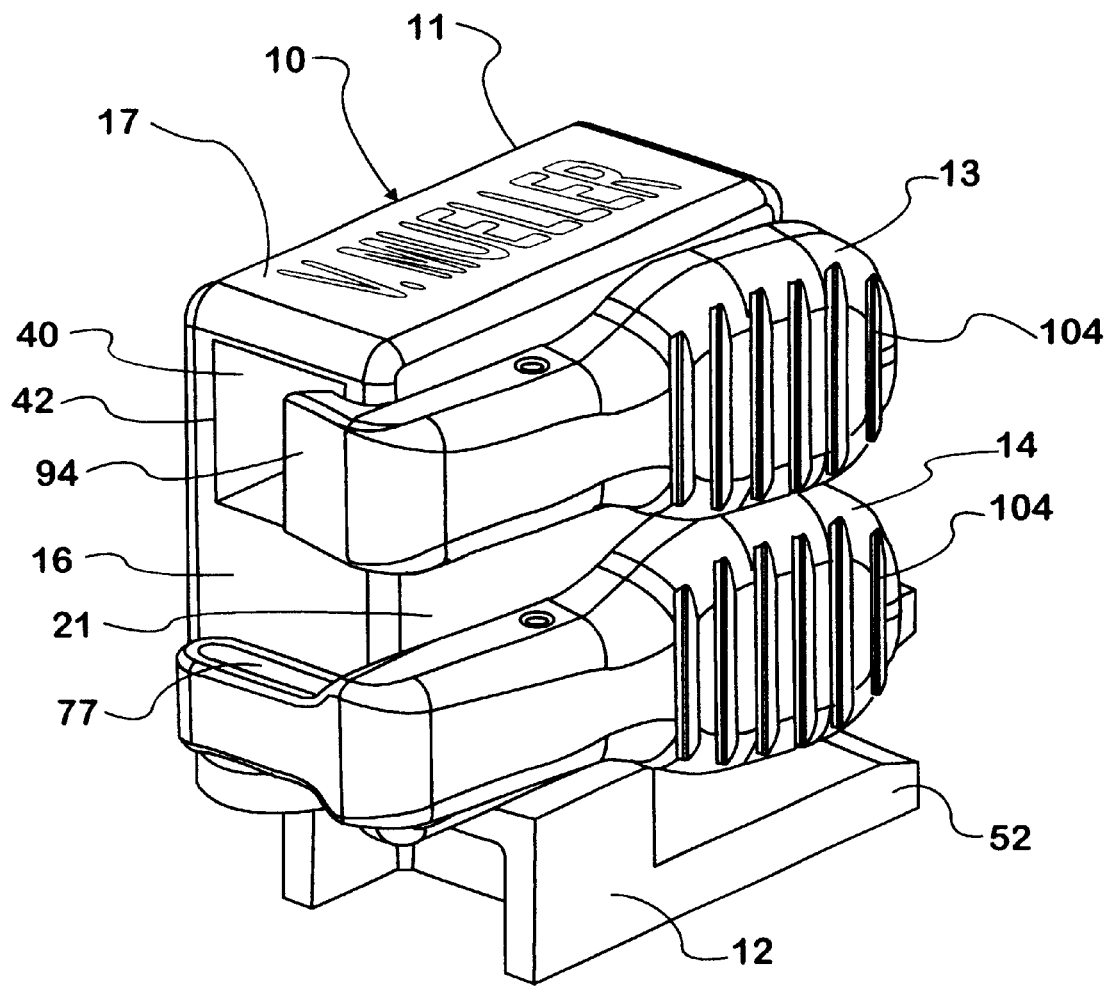
FIG. 4 is an angled side view of the device from the rear showing the side containing the adjustment tabs according to one embodiment of the invention.
Figure 5:
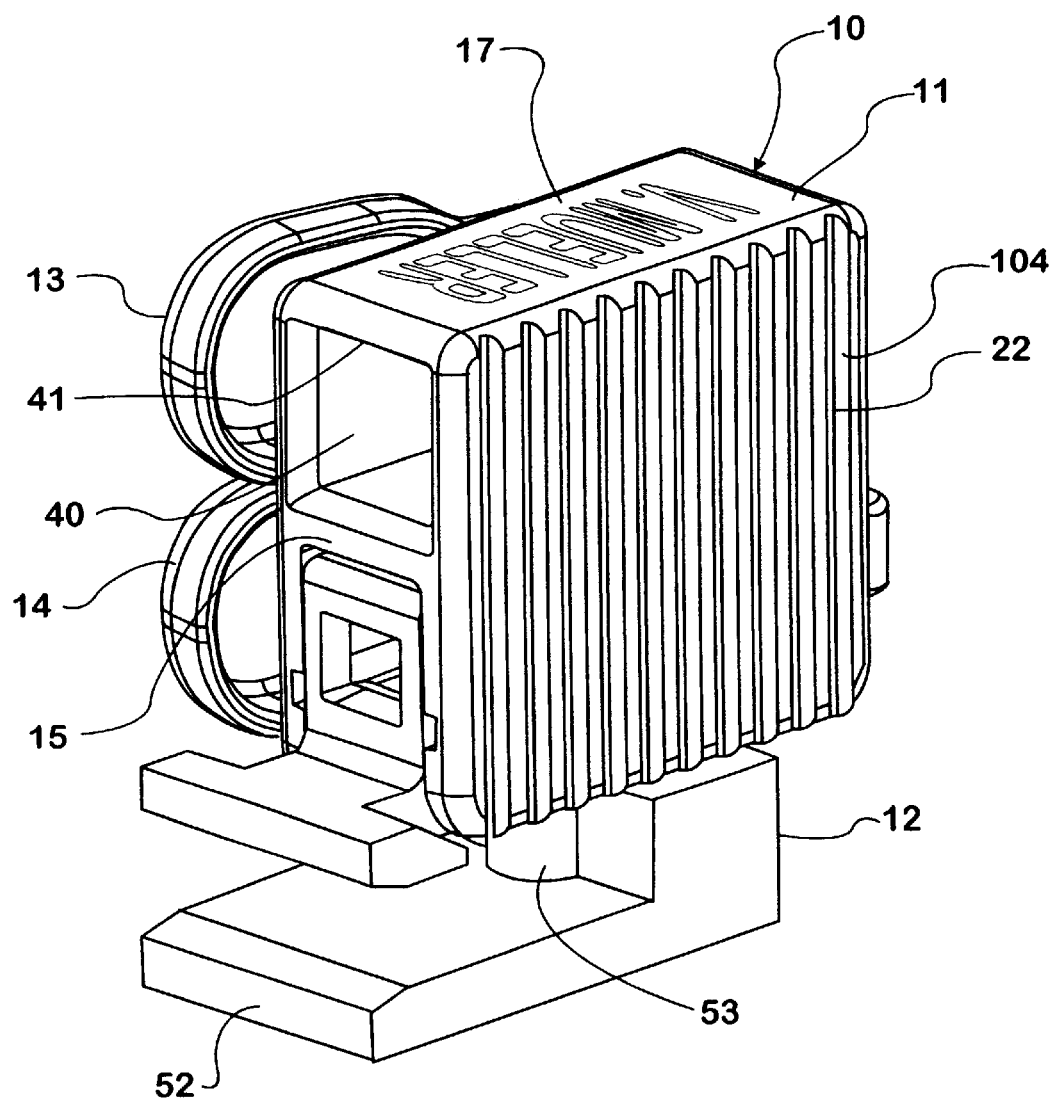
FIG. 5 is an angled side view of the front of the device from the opposing side to that shown in FIG. 4 according to one embodiment of the invention.
Figure 6:
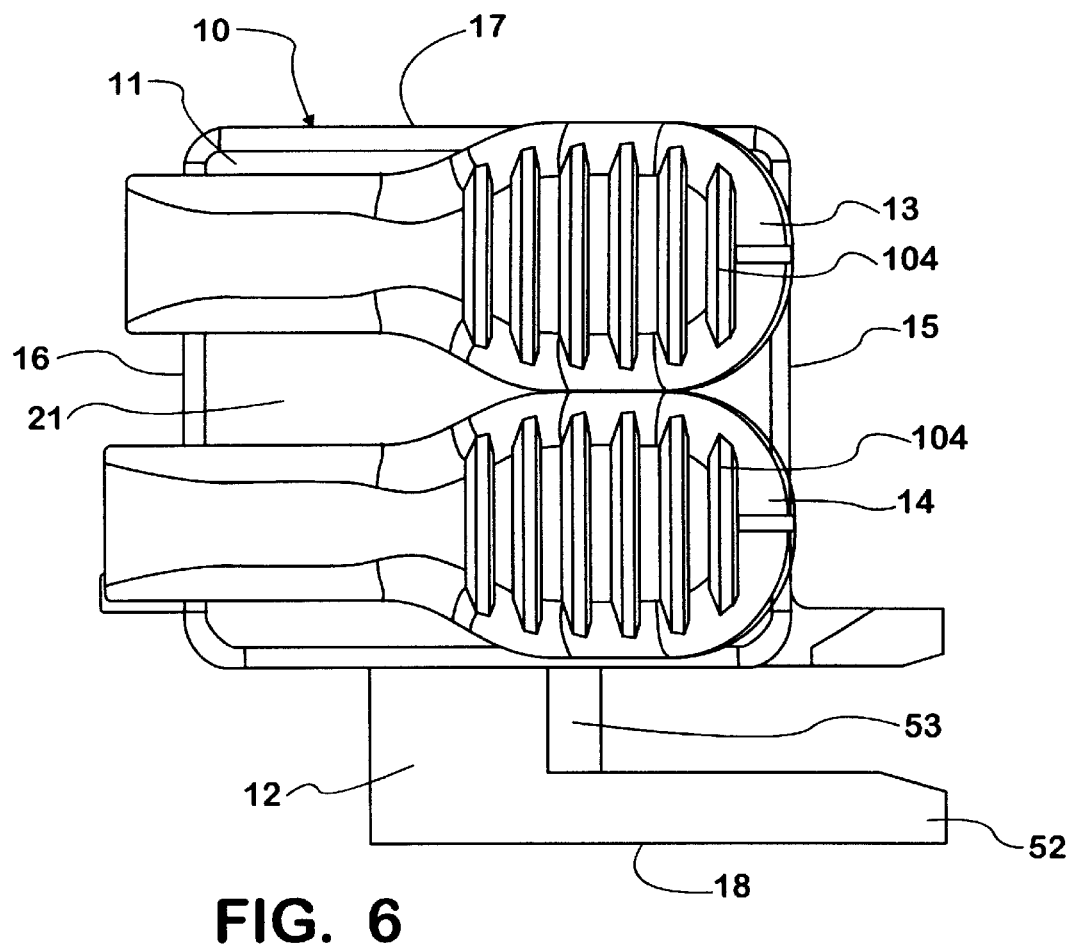
FIG. 6 is a side view of the device of the side containing both adjustment tabs according to one embodiment of the invention.
Figure 7:
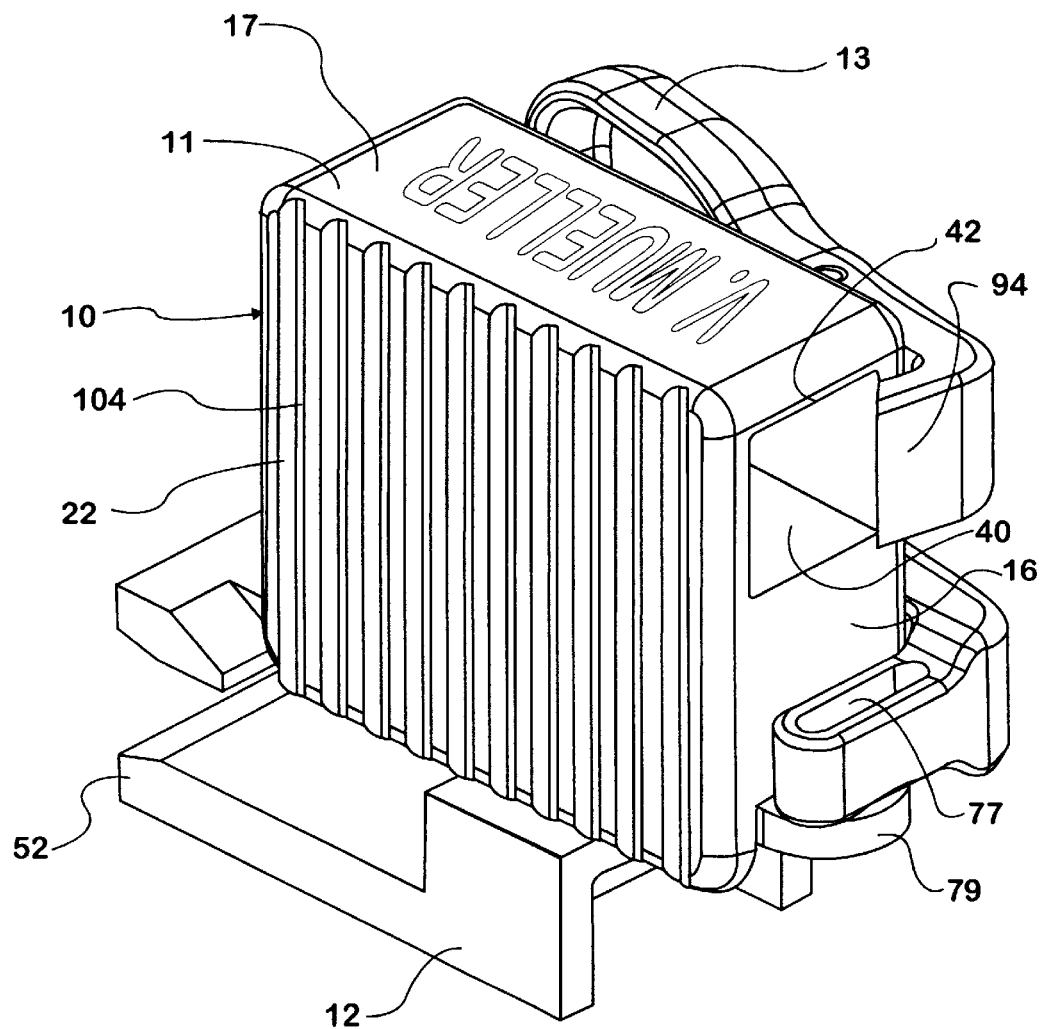
FIG. 7 is an angled side view from the rear of the device showing the side without the adjustment tabs according to one embodiment of the invention.
Figure 8:
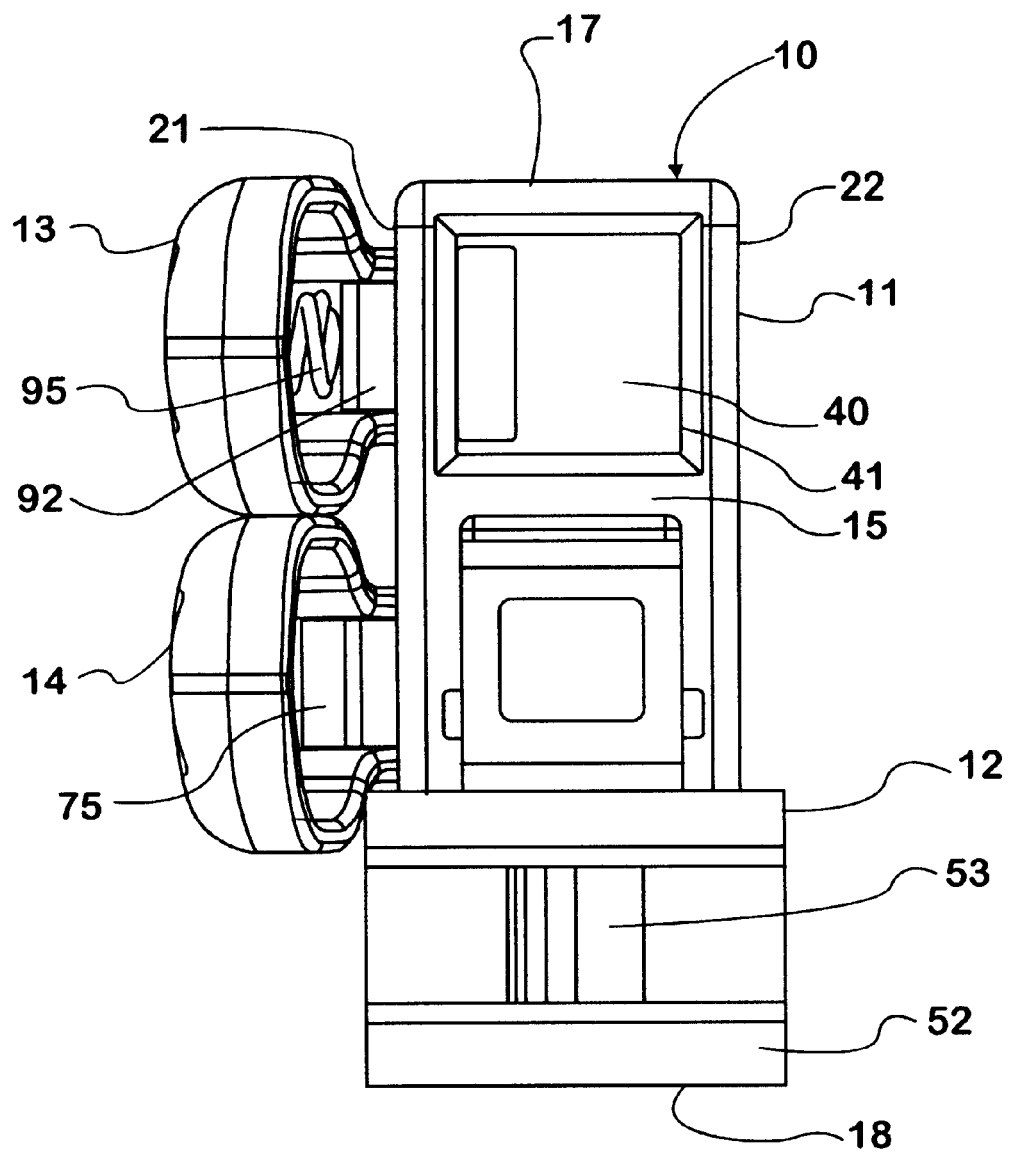
FIG. 8 is a front view of the device according to one embodiment of the invention.
Figure 9:
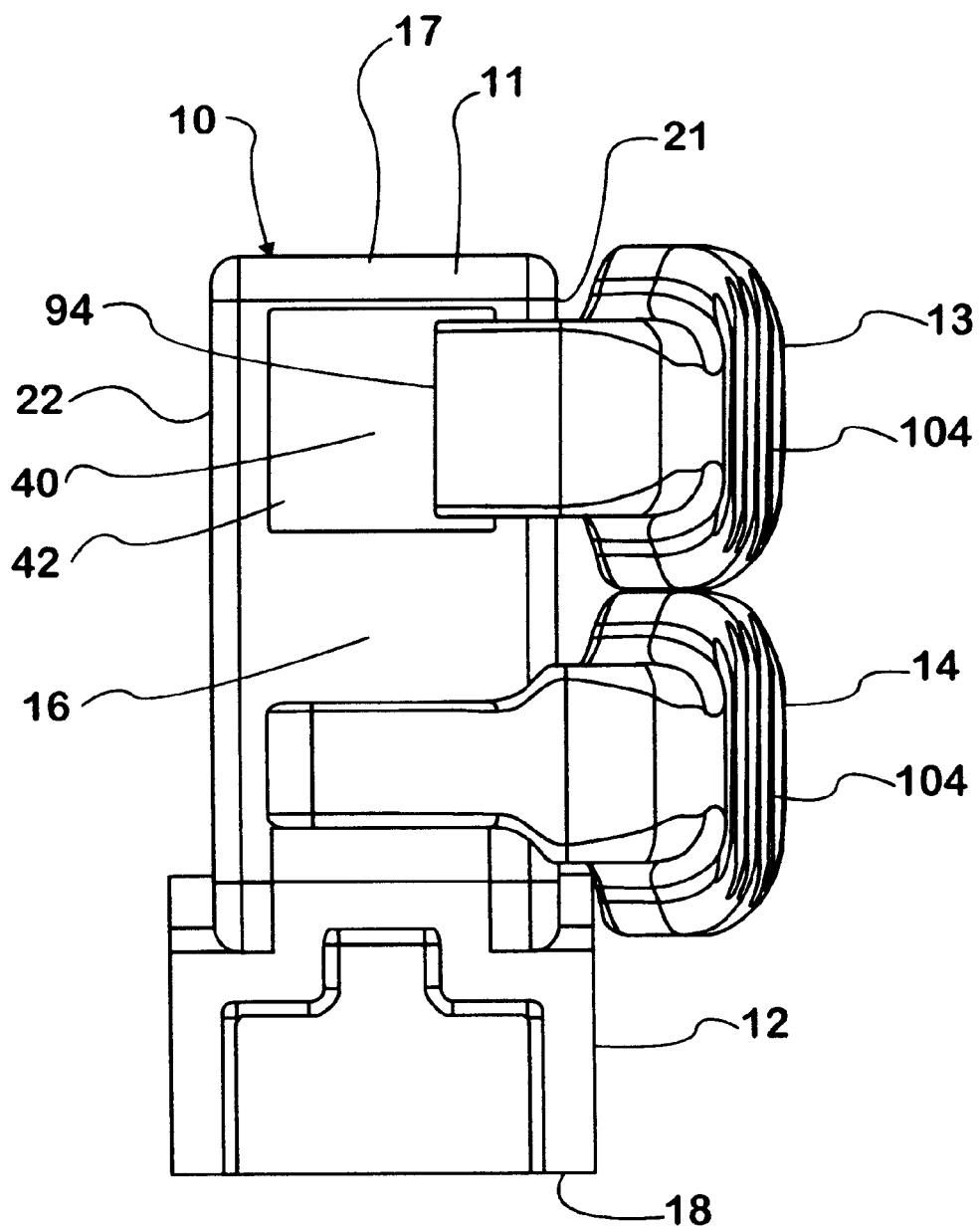
FIG. 9 is a rear view of the device according to one embodiment of the invention.
Figure 10:
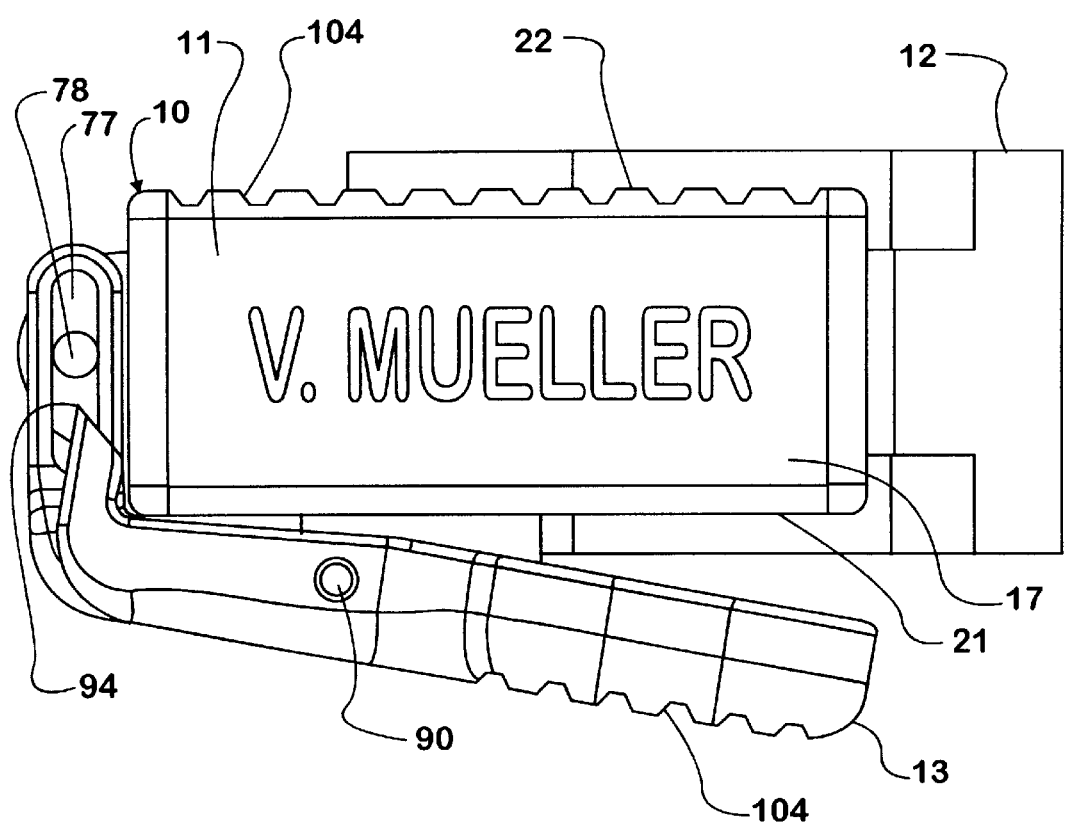
FIG. 10 is a top view of the device according to one embodiment of the invention.

The movable portion 11 of the housing is adapted to accommodate a retractor blade stem 31 within. As illustrated in FIGS. 4, 5, 7 through 9 and 11, the movable portion 11 of the housing 10 comprises a channel 40 which terminates at a front end opening 41 and a rear end opening 42 and which aligns with the longitudinal axis of the retractor blade stem 31, the channel 40 being dimensioned to accommodate the height and width of the stem 31. The exterior surface of the blade stem can comprise a surface structure adapted to interact with the longitudinal adjustment mechanism components to secure the longitudinal position of the stem (and thus, the blade attached to the end of the stem). One such a surface structure is illustrated in FIGS. 1 through 3 as a series of ridges 51.

The support portion 12 of the housing 10 is movably coupled to the movable portion 12 of the housing and is adapted to accommodate a portion of a retractor support structure 20 and secure the device thereon. The front end of the support portion 12 of the housing can be structured to comprise a bracket 52 to surround the upper and lower surfaces of the retractor support structure 20. The support portion 12 of the housing can be adapted to permit incremental positioning in the lateral direction along the retractor support structure 20 in an assembly as depicted in FIGS. 2 and 3, for example. In one embodiment and as shown in FIGS. 5, 6, 7, 15A and 15B, a portion of the support portion 12 of the housing can comprise a rib 53 which extends outward from within the bracket and coordinates with a series of notches 55 positioned along the perimeter of retractor support structure 20. In use, the force of the patient's tissue against retractor blade 30 translates into resistance forces against outward migration of the device which would separate the device apart from the retractor support structure 20.

Figure 15B:
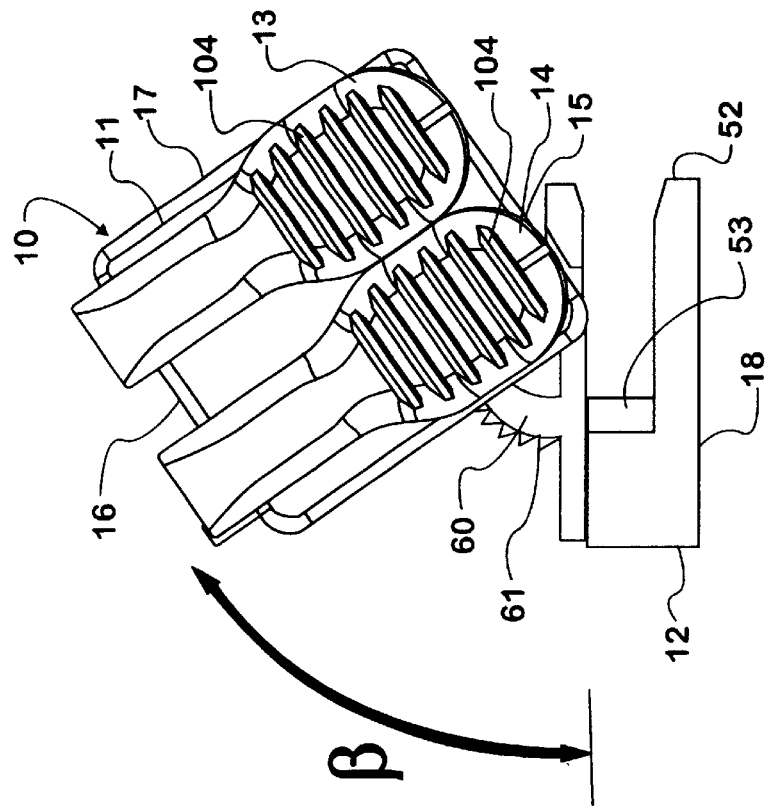
FIGS. 15A and 15B are two side views of the device which together illustrate the longitudinal and tilting adjustment motion of the device respectively according to one embodiment of the invention.

Referring now to FIG. 11, the upper surface of the support portion 12 of the housing can comprise a tilt ratchet 60 to provide the incremental adjustment of the movable portion 11 of the housing relative to the support portion 12. The tilt ratchet 60 can be in the configuration of parallel ridges 61 as shown in FIGS. 11 and 15B which extend into the interior of the movable portion 11 of the housing 10 to interact and engage a portion of the tilt adjustment mechanism. Various other structures which can function as a "ratchet" or incremental adjustment mechanism can be used as well, including holes, grooves, indentations, nodules, and the like, provided they are structure to engage the tilt adjustment mechanism component(s).

Referring now to FIG. 11, the movable portion 11 of the housing 10 and the support portion 12 of the housing of the device are coupled by a hinge structure. Such a hinge structure can include a hinging pin 70 which is inserted in alignment through openings 71 and 72 located in both the movable portion 11 of the housing and support portion 12 of the housing respectively, and movably couples the housing portions to one another. The hinging pin 70 by virtue of its location functions as the axis of radial tilting movement of the movable portion 11 of the housing relative to the support structure 12.

The tilt adjustment tab 14 is mechanically coupled to the remaining components collectively referred to as the tilt adjustment mechanism, which is controls the angular-vertical tilt position of the movable portion 11 of housing relative to the support portion 12. This tilt movement is illustrated in FIG. 15B and represented by the symbol beta ($\beta$).

Referring again to FIG. 11, analogous components for the alternative embodiment (having adjustment tabs on opposing sides) are illustrated in FIG. 14 as well, both the longitudinal adjustment tab 13 and tilt adjustment tab 14 are structured to respond to pressure exerted by a fingertip and actuate the corresponding adjustment mechanisms. The tilt adjustment tab 14 of the tilt adjustment mechanism is hingedly coupled to the movable portion 11 of the housing. The tilt hinge structure is shown as a tilt pivot pin 73 inserted in alignment through an opening 74 through a first protrusion 75 extending from the body of the movable portion 11 of the housing 10 and openings 76 in the medial portion of the tilt adjustment tab 14 body. The distal portion (relative to the finger contacting portion) of the tilt adjustment tab 14 contains a slot 77 which receives and interacts with an actuation stem 78 located on the platform 79 of the sliding latch 80. Interior of the movable portion 11 of the housing accommodates and retains the sliding latch 80 so as to permit sliding motion toward and away from the front and rear sides of the housing, 15 and 16 respectively. The opposite end of the sliding latch 80 contains a wedge 81 which is configured to engage the ridges 61 of the tilt ratchet 60 of the support portion 12 of the housing. The sliding latch 80 interacts in turn with a first biasing element 82. In the Figures, the first biasing element 82 is shown as a spring which interacts with a biasing element receiver 83 on the sliding latch 80. The first biasing element 82 interacts with both the sliding latch 80 and interior of the rear side wall of the device to bias the tilt adjustment mechanism into the engaged position. The opposing force to the biasing element and actuation of the tilt adjustment mechanism is produced by the physical force exerted on the tilt adjustment tab 14 finger contacting portion. The pivoting action of the tilt adjustment tab 14 pivots the tab so as to pull the sliding latch 80, by way of the actuation stem 78, in a rearward direction thereby disengaging the wedge 81 from a ridge 61 on the tilt ratchet 60. Once disengaged, the device can be tilted to adjust the vertical angle $\beta$ of the device as shown in FIG. 15B along with the retractor blade in the surgical site. Likewise, release of such force re-engages the tilt ratchet at the most recent position. The device of the invention can be constructed to permit a vertical tilt adjustment angle $\beta$ ranging from 0° to about 90° relative to the horizontal plane of the support structure 12 of the housing and retractor support structure when attached.

Figure 15A:
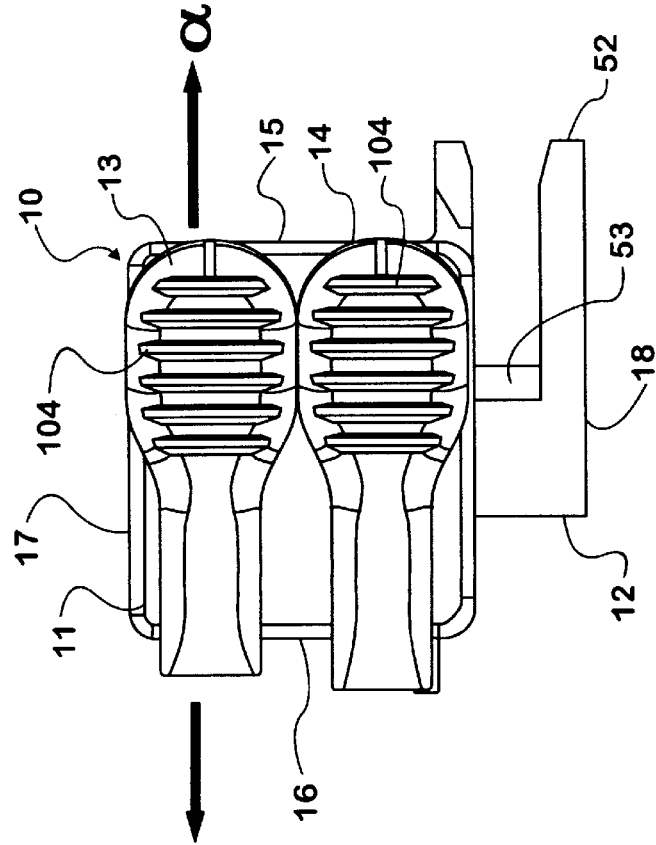

The longitudinal adjustment tab 13 is mechanically coupled to the remaining components collectively referred to as the longitudinal adjustment mechanism, which controls the incremental movement along the longitudinal axis of the retractor blade stem 31 relative to the movable portion of the housing. This longitudinal movement is illustrated in FIG. 15A and represented by the symbol alpha ($\alpha$).

Referring again to FIG. 11, the longitudinal adjustment tab 13 of the longitudinal adjustment mechanism is hingedly coupled to the movable portion 11 of the housing 10. As a practical matter of design, the longitudinal adjustment tab 13 is preferably located nearest the upper side of the device alongside the channel 40 which accommodates the retractor blade stem 31. Such a position affords the greatest range of motion for tilt adjustment without structural interference of other components. The longitudinal hinge structure is shown as a longitudinal pivot pin 90 inserted in alignment through an opening 91 through a second protrusion 92 extending from the movable portion 11 of the housing and openings 93 in the medial portion of the longitudinal adjustment tab 13 body. The distal portion (relative to the finger contacting portion) of the longitudinal adjustment tab 13 contains a hook 94. Hook 94 interacts with the corresponding ridges 51 on the retractor blade stem 31 (see FIGS. 2 and 3, for example). The longitudinal adjustment tab 13 interacts with a second biasing element 95. The second bias element 95 is shown in the form of a spring. The second biasing element 95 is located between the tab and a second biasing element receiver 96 on the movable portion 11 of the housing 10. The opposing force to the second biasing element 95 and actuation of the longitudinal adjustment mechanism is produced by the physical force exerted on the longitudinal adjustment tab 13 finger contacting portion. The pivoting action of the longitudinal adjustment tab 13 pivots the tab so as to move the hook 94 in a direction away from the retractor blade stem 31, thereby disengaging the ridge 51 of the retractor blade stem 31. Once disengaged, the blade stem 31 can be moved freely along its longitudinal axis a in a forward or rearward direction as represented in FIG. 15A. Likewise, release of such force re-engages the retractor stem ratchet in the most recent position.

An alternative and less preferred embodiment of the device of the invention is shown in FIGS. 12 through 14, in which the tilt adjustment tab 14b is positioned on the opposing side of the movable portion 11b of the housing 10b from the longitudinal adjustment tab 13b. Otherwise, the adjustment mechanism components are analogously illustrated by the same numerical references followed by the letter "b". Whereas the index and middle fingers would contact the tabs in the device having the tabs on the same side, in this embodiment the thumb would contact one of the tabs and either the index or middle finger would contact the other tab. As with the same-side positioned tab embodiment, the comfortable, natural "pinching" configuration of one of the user's hand is employed to operate the device.

Although depicted as springs, a variety of biasing element structures can be used in accordance with the invention. Any resilient structure which can be positioned between the components described and exert a force which can be overcome by forces exerted by a finger can be used. Such biasing structures include, but are not limited to, flexible plastic or metallic crimped or pleated components, and the like.

In accordance with the invention, each of the adjustment mechanisms is constructed to permit individual or simultaneous actuation alongside the other. By virtue of its construction and design, individual or simultaneous actuation of the adjustment mechanisms is performed by simple, comfortable and minor movements by the user's fingers on a single hand.

The components of the ratchet device of the invention can be composed of any conventional material in the art having enough structural rigidity to perform the intended function. Preferably, the components of the device are composed of sterilizable materials. Materials which can be used in the device of the invention include plastics, metals and metallic alloys, or combinations of both, which are readily available in the medical device manufacturing field. In other words, some components of the same device can be composed of different materials. Metals and metallic alloys which can be used include, but are not limited to, stainless steel, titanium, and the like. One or more of the individual components of the device can be manufactured by conventional machining or injection molding techniques. The device of the invention can be constructed for either left handed or right handed operation in accordance with the intended user's dexterity.

In a general surgical procedure, once a patient has been prepped for surgery and the incision has been made, a retractor assembly is positioned such that at least a portion of the retractor support structure circumscribes and surrounds the incision site to be opened. The retractor device of the invention is attached to the stem portion of the retractor blade, and the blade is inserted into the incision site. The retractor device is then secured to the desired location on the retractor support structure. Interaction between the blade and tissue of the toe-in movement at the operative site provides the tension forces which secure the support portion of the device onto the support structure, e.g., ring assembly. The toe-in positioning of the retractor blade is adjusted by the practitioner by the independent or simultaneous tilt adjustment and longitudinal adjustment mechanisms of the device in accordance with the invention. One or more retractor blades attached to a corresponding number of retractor devices of the invention can be used, or a combination of the retractor device of the invention with conventional retractor assemblies can be used in a single procedure.

Industrial Applicability

The device of the invention is useful in surgical procedures that utilize retractors to restrain the tissue surrounding the surgical site to permit unobstructed access thereto. The invention improves the user's ability to independently or simultaneously adjust multiple positions of the retractor, namely the longitudinal axial position of the retractor blade stem and the angular, vertical tilt relative to a horizontal plane. This is accomplished in a single-handed operation and reduces awkward maneuvering of the hand and fingers. The device of the invention therefore facilitates the accuracy or precision of the retractor position in the patient.

The invention has been described with reference to various specific and preferred embodiments and techniques. It will be understood that a variety of adjustments and modifications can be made to the various embodiments and techniques while remaining within the spirit and scope of the invention as defined by the claims set forth below.

What is claimed is:

1. A multipositional ratchet device for use with a surgical retractor comprising:
    a) a housing adapted to accommodate a portion of a retractor blade stem, said housing having a front end and rear end and two opposing sides, a movable portion movably coupled to a support portion;
    b) tilt adjustment mechanism mechanically coupled to said housing and adapted to control the vertical tilt position of said movable portion of housing relative to said support portion of said housing;
    c) longitudinal adjustment mechanism mechanically coupled to said housing and adapted to control the longitudinal axial positioning of said retractor blade stem relative to said housing;
    wherein said tilt adjustment mechanism comprises a tilt adjustment tab and said longitudinal adjustment mechanism comprises a longitudinal adjustment tab, said adjustment tabs permitting both independent and simultaneous tilt and longitudinal adjustments respectively, said mechanisms being mechanically independent of one another, using continuously maintained finger contact thereon by a single hand throughout said adjustment;
    and wherein said tilt adjustment tab and longitudinal adjustment tab are located on the same side of said housing with the finger pads of said adjustment tabs adjacent one another to permit both adjustments to be operated with the index finger and third finger of the same hand.

2. The multipositional ratchet device according to claim 1 wherein said movable portion of the housing and support portion of the housing are coupled by a hinging structure.

3. The multipositional ratchet device according to claim 1 wherein said support portion of the housing comprises a tilt ratchet providing incremental angular vertical tilt adjustment of said movable portion of said housing relative to the support portion.

4. The multipositional ratchet device according to claim 3 wherein said incremental angular vertical tilt adjustment is controlled by said tilt adjustment tab.

* * * * *